United States Patent [19]

Ohki et al.

[11] Patent Number: 5,752,505
[45] Date of Patent: May 19, 1998

[54] INHALATION-TYPE MEDICINE DELIVERY DEVICE

[75] Inventors: Hisatomo Ohki; Shigemi Nakamura; Kazunori Ishizeki; Yoshiyuki Yazawa, all of Gunma; Akira Yanagawa, Yokohama, all of Japan

[73] Assignees: Unisia Jecs Corporation, Atsugi; Dott Limited Company, Yokohama, both of Japan

[21] Appl. No.: 820,654

[22] Filed: Mar. 18, 1997

[30] Foreign Application Priority Data

Mar. 21, 1996 [JP] Japan ................ 8-092024

[51] Int. Cl.$^6$ .............................................. A61M 15/00
[52] U.S. Cl. ........................ 128/203.15; 128/203.21
[58] Field of Search ...................... 128/200.14, 203.12, 128/203.15, 203.21; 604/58

[56] References Cited

U.S. PATENT DOCUMENTS

| | | | |
|---|---|---|---|
| 3,906,950 | 9/1975 | Cocozza | 128/203.21 |
| 3,918,451 | 11/1975 | Steil | 128/203.21 |
| 3,991,761 | 11/1976 | Cocozza | 128/203.21 |
| 4,069,819 | 1/1978 | Valentini et al. | 604/58 |
| 4,423,724 | 1/1984 | Young | 604/58 |
| 4,889,114 | 12/1989 | Kladders | 604/58 |
| 5,201,308 | 4/1993 | Newhouse | 128/203.21 |
| 5,327,883 | 7/1994 | Williams et al. | 128/203.21 |
| 5,349,947 | 9/1994 | Newhouse et al. | 128/203.21 |
| 5,619,985 | 4/1997 | Ohki et al. | 128/203.21 |
| 5,647,349 | 7/1997 | Ohki et al. | 128/203.21 |

*Primary Examiner*—Aaron J. Lewis
*Attorney, Agent, or Firm*—Foley & Lardner

[57] ABSTRACT

An inhalation type medication delivery device includes a dispenser body having a powder containment chamber at one axial side thereof and an inhalation port for drawing in a powder type medication on the another. An attached lid is provided on the dispenser body for opening and/or closing the powder containment chamber. In addition, an air passage is defined in the body allowing a powder type medication to be introduced into an airflow toward the inhalation port according to inhalation by a user. One end of the air passage opens through the lid towards the outside atmosphere and the other end communicates with the inhalation port while passing through the powder containment chamber. Also, a check valve is installed in the lid to prevent air drawn into said inhalation port from flowing in an outward direction opposite a medication delivery direction toward the inhalation port. Additional efficiency may be achieved by further providing a supplementary passage communicating between the inhalation port and the outside atmosphere independently of the air passage to generate additional suction force during inhalation.

11 Claims, 9 Drawing Sheets

INHALATION-TYPE MEDICINE DELIVERY DEVICE

BACKGROUND OF THE INVENTION

This invention relates to an inhalation type medication delivery device which can be conveniently used when, for example, a powdered type of medication is to be applied to the bronchial and/or respiratory areas via inhalation. For example, for directly applying medication in measured doses to the lungs for treatment of asthma or the like.

DESCRIPTION OF THE RELATED ART

Delivery methods for bronchial and respiratory medication generally include, injection, intravenous drip, and direct application via inhalation of an aerosol spray using a carrier gas or with a nebulizer for delivering powder form medication from a powder storing chamber or a capsule in such a way as to be inhaled by the patient.

Of these methods for applying a powder to asthmatic patients, the one whereby the powder is filled into a capsule to be inhaled by the patient achieves the object in this way: an inhalator is prepared which has an inhalation port to be put into the mouth of the patient, and has, in its interior, a passage whose one end opens its mouth to the atmosphere and the other end communicates through a capsule carrying chamber with the inhalation port; the capsule is penetrated with, for example, a boring needle, so that a hole is made which communicates with the passage. If in this state the patient puts the inhalation port in his mouth, and breathes in, the powder in the capsule will be released into the inhalation port by the air current flowing through the passage, and drawn into the lungs of the patient.

As described above, in the conventional inhalator adapted for capsulated medicines, inhalation of powder takes place by allowing the patient to draw in air through the inhalation port.

However, when a patient inhales such powder type medication, it often provokes coughing, in which case air is blown into the inhalation port through the passage in a direction opposite to the delivery direction. The powder in the capsule, therefore, will be blown out into the air. As a result, the inhaled dosage may vary from the prescribed amount and maximum efficacy of the treatment cannot be expected.

The present invention has been proposed as a remedy for the above problem inherent to conventional inhalators, and intends to provide an inhalation type medication delivery device which is capable of preventing powder form medication from carrying from a chamber or capsule in a direction other than the intended delivery direction. The present invention further provides an inhalation type medication delivery device which consistently provides such powder type medication is measured for safety and optimum efficacy for the patient.

SUMMARY OF THE INVENTION

Thus, it is an object of the present invention to overcome the drawbacks of the related art.

It is a further object of the invention to provide a

According to one aspect of the invention, there is provided an inhalation type medication device comprising: a dispenser body which has a powder containment chamber disposed at a first axial side therof and an inhalation port for drawing in a powder type medication on a second axial side thereof; a lid for opening/closing the powder containment chamber; an air passage defined in the dispenser body for allowing introduction of the powder type medication in the powder containment chamber of the dispenser body into an airflow toward the inhalation port according to a suction force generated by inhalation, one end of the air passage opening through the lid towards an ambient atmosphere and another end of which communicates through the powder containment chamber with the inhalation port; and a check valve which is installed into the lid to prevent air drawn into the inhalation port from flowing through the air passage towards the ambient atmosphere.

The above described construction permits the patient to inhale powder through following processes: to introduce powder into the powder containment chamber, he opens the lid leading to the powder containment chamber, and, after he has filled the powder containment chamber with a powder, closes the lid. This operation prevents the powder from falling or escaping from the powder containment chamber. Then, to inhale the powder stored in the powder containment chamber, the patient puts the inhalation port into his mouth, and breathes in air, which makes powder in the powder containment chamber move through the inhalation port into the lungs of the patient. If, during this operation, the patient by accident makes coughs while putting the inhalation port in his mouth, and this makes air in the inhalation port flow in the opposite direction to normal, this counter air current will flow through the air passage and meet the check valve installed in the lid which, by being activated with the counter air current, will close, thereby preventing powder in the powder containment chamber from escaping towards the atmosphere.

Another aspect of the invention is characterized by adding a supplementary air passage to the dispenser body which interconnects the atmosphere and the inhalation port independently of the air passage, to permit the user to draw in additional air while he is inhaling powder.

Further, there is provided according to another aspect of the invention an inhalation type powdered medication delivery device comprising a dispenser body including a capsule carrying chamber disposed at a first axial end thereof for retaining a capsule filled with a powder type medication and, an inhalation port for facilitating inhalation of the powder type formed at a second axial end of the dispenser body; a lid for opening/closing the powder containment chamber; an air inflow passage defined in the dispenser body such that a first end thereof opens through the lid towards and ambient atmosphere and a second end thereof is communicated with the inhalation port; piercing means attached to the dispenser body; and a capsule insertable in the capsule carrying chamber, the capsule having an opening defined therein according to utilization of the piercing means, the opening so formed as to establish communication between an interior of the capsule and a portion of the air inflow passage when the capsule is positioned in the capsule carrying chamber; a check valve provided at the lid to prevent air drawn into the inhalation port from flowing through the air inflow passage in a direction other than an air inflow direction.

The above construction permits the patient to inhale powder through following processes: to introduce a capsule filled with powder into the powder containment chamber, the patient opens the lid leading to the capsule carrying chamber, and, after he has introduced the capsule into the capsule carrying chamber, closes the lid. This operation prevents the capsule from falling or escaping from the capsule carrying chamber. Through the capsule in the capsule carrying chamber is punctured with the piercing member which communicates with both the air inflow and air outflow passages. Then, to inhale powder stored in the capsule in the capsule carrying chamber, the patient puts the inhalation port into his mouth, and breathes in air, to allow air to flow through the air inflow passage into the capsule, which makes powder in the capsule move from the air outflow passage through the inhalation port into the lungs of the patient. If, during this operation, the patient by accident makes coughs while putting the inhalation port in his mouth, and this makes air in the inhalation port flow in the opposite direction to normal, the counter air current in the inhalation port will flow from air outflow passage through the capsule and then towards the air inflow passage. At that time the check valve installed in the lid will be put to closure, so that escape of powder in the capsule into the atmosphere under the influence of the counter air flow will be prevented.

In addition, according to yet another aspect of the invention, there is provided an inhalation type powdered medication delivery device comprising: a dispenser body including a powder containment chamber disposed at a first axial end thereof, and an inhalation port for facilitating inhalation of a powder type medication formed at a second axial end thereof; a lid for opening/closing the powder containment chamber; an air inflow passage defined in the dispenser body and having a first end thereof disposed at the lid so as to be communicated with an ambient atmosphere, a second end thereof being formed so as to communicate with the inhalation port; an air outflow passage defined in the dispenser body and having a first end thereof disposed at the powder containment chamber, a second end thereof being formed so as to communicate with inhalation port; a supplementary passage which communicates between the inhalation port and the ambient atmosphere independently of the air inflow and the air outflow passages, so as to generate a supplementary air suction action during inhalation of the powder type medication; a common air passage formed in the lid and having a first end thereof opening to the ambient atmosphere and a second end thereof in communication with the air inflow, air outflow and supplementary air passages; and a check valve installed into the lid and placed substantially midway along the common air passage, to prevent air drawn into the inhalation port from flowing from the air outflow passage through the powder containment chamber or through the air inflow passage toward the ambient atmosphere.

According to this arrangement the inhalation type medication delivery device permits the patient to inhale powder through following processes: to introduce powder into the powder containment chamber, he opens the lid leading to the capsule carrying chamber, and, after having filled the powder containment chamber with powder, closes the lid. This operation prevents powder from falling or escaping from the powder containment chamber. Then, to inhale powder stored in the powder containment chamber, the patient puts the inhalation port into his mouth, and breathes in air, to allow air to flow from the common air passage through the air inflow passage into the powder containment chamber, which makes powder in the powder containment chamber move from the air outflow passage through the inhalation port into the lungs of the patient. If, during this operation, the patient by accident makes coughs while putting the inhalation port in his mouth, and this makes air in the inhalation port flow in the opposite direction to normal, the counter air current in the inhalation port will flow from air outflow passage through the powder containment chamber and then towards the air inflow passage. At that time the check valve installed in the lid and placed midway of the common air passage will be put to closure, so that escape of powder in the powder containment chamber into the atmosphere under the pressure of the counter air flow will be prevented.

DESCRIPTION OF THE PREFERRED EMBODIMENT

Figure 1:
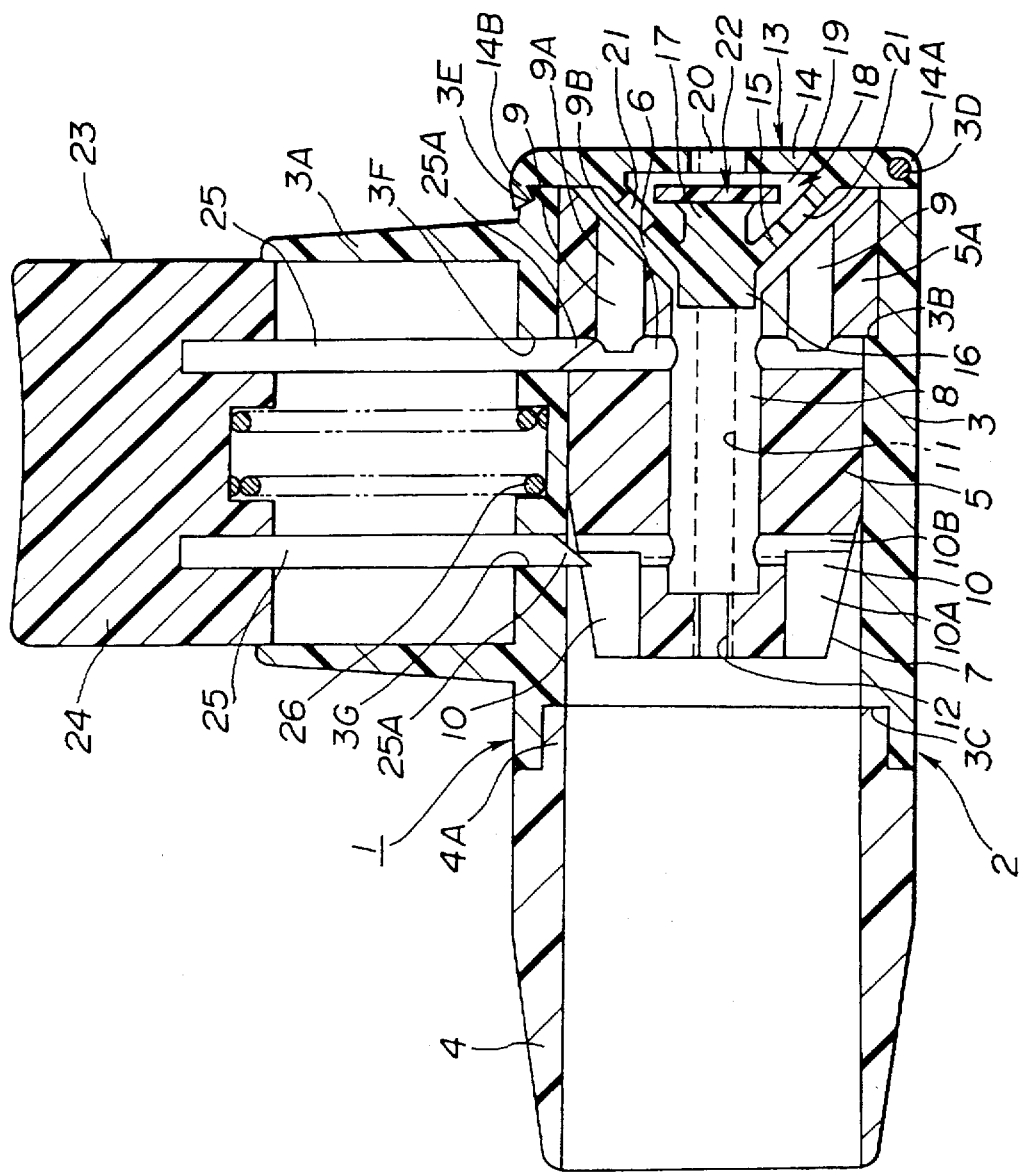
FIG. 1 is a sectional view of the inhalation type medication delivery deviceof the first preferred embodiment according to this invention.

Preferred examples of the inhalation type medication delivery deviceof this invention will be detailed below with reference to attached figures.

FIGS. 1–4 illustrates the first example of this invention.

In the figures, 1 represents a dispenser body which forms the body of the present inhalation inhalation type medication delivery device. This dispenser body 1 consists of an dispenser body 2 and a capsule holder 5 which will be described later.

The main portion of the inhalation type medicine delivery device is a substantially cylindrical dispenser body 2. The dispenser body 2 essentially consists of a holder carrier 3 which is positioned on one side (top side) of the dispenser body and holds a capsule holder 5 in its interior, and of a below-described inhalation port 4 which is arranged on the other side (mouth side) of the holder carrier 3. On the side wall of the holder carrier 3 is attached a guide cylinder 3A having an outward protruding mouth, and into that cylinder a support 24 of a below-described piercing member 23 is inserted movable. On one side of the holder carrier 3, is formed an annular step 3B which engages with a stopper 5A of the capsule holder 5, while on the other side, is formed an annular step 3C which engages with a fitting cylinder 4A of the inhalation port 4. In addition, on the periphery of top side of the holder carrier 3, are prepared a bracket 3D which protrudes in an axial direction and joins with the body 14 of a below-described cap 13, and on the opposite side of the same periphery a notch 3E which engages with a jointing nail 14B. In the wall of the holder carrier 3 forming the bottom of the guide cylinder 3A, two holes are opened radially, one hole or a pin mortise 3F at a position corresponding with a pin insertion mortise 9B of a below-described air inflow passage 9, and the other hole or a pin mortise 3G at a position corresponding with a pin insertion mortise 10B of an air outflow passage 10.

An inhalation port 4 is prepared on the mouth side of the holder carrier 3 and forms, together with the holder carrier 3, the dispenser body 2. On one end of the inhalation port 4 is jointed as a unit the fitting cylinder 4A which reversibly fits to the annular step 3C of the holder carrier 3. The inhalation port 4 forms a means by which the patient takes in powder type medication from the mouth.

Figure 2:
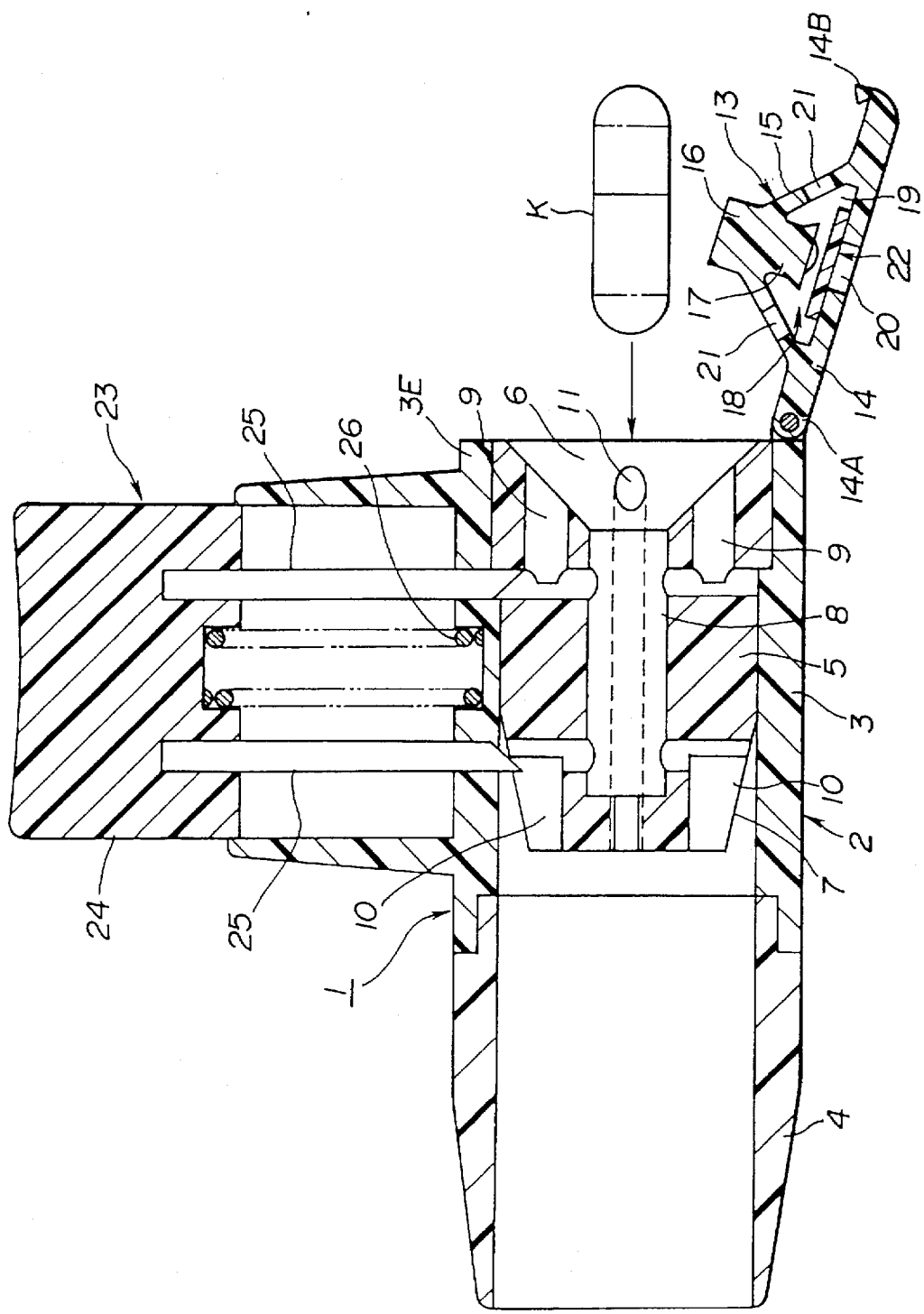
FIG. 2 is another sectional view seen from the same angle as in FIG. 1 which illustrates how a capsule is introduced into the capsule carrying chamber after the cap has been opened.

A capsule holder 5 is inserted into the interior of the holder carrier 3. The capsule holder 5 is shaped practically like a column, and has an annular stopper 5A formed on the periphery on top side which, by engaging with the annular stopper 3B of the holder carrier 3, puts the capsule holder 5 into a proper position within the cavity of the holder carrier 3. On top side of the capsule holder 5, is prepared a capsule insertion guide 6 which forms, as shown in FIG. 2, a conical cavity which has its diameter increasingly contracted towards mouth side. The periphery on mouth side of the capsule holder 5 takes a conical form whose circumference 7 increasingly contracts towards the inhalation mouth.

A powder containment chamber 8 (or capsule carrying chamber 8) is prepared in the axial direction at the center of the capsule holder 5, and has a hole opened on top end which communicates with the capsule insertion guide 6. The capsule carrying chamber 8 holds a capsule K inserted through the hole opened on its top end, and is so constructed that, when the capsule has been put into place, its open end is closed by a capsule stabilizer 16 of the cap 13. The capsule has a long cylindrical form and contains a powder type medication in its interior.

Two air inflow passages 9, 9 are prepared on the top side of the capsule holder 5. The air inflow passages 9, 9 are composed each of two components, or inlets 9A, 9A and pin insertion mortises 9B, 9B: the inlet 9A is prepared axially in the capsule holder 5 near the periphery, and opens its mouth on the capsule insertion guide 6; and the pin insertion mortise 9B is so prepared as to communicate with the inlet 9A and to open its mouth to the capsule carrying chamber 8. Each of the pin insertion mortises 9B communicates with the corresponding pin mortise 3F prepared in the wall of the holder carrier 3.

Two air outflow passages 10, 10 are prepared at the mouth side of the capsule holder 5. The air outflow passages 10, 10 are composed each of two components, or outlets 10A, 10A and pin insertion mortises 10B, 10B: the outlet 10A is prepared by removing part of the conical wall 7 of the capsule holder 5 surrounding the periphery of the capsule carrying chamber 8, and the pin insertion mortise 10B is so prepared radially in the capsule holder 5 as to communicate with the outlet 10A and to open its mouth to the capsule carrying chamber 8. Each of the pin insertion mortises 10B communicates with the corresponding pin mortise 3G prepared in the wall of the holder carrier 3.

The air inflow passages 9, when air is drawn in by inhalation from the inhalation port, allows the air to enter through a below-described common air passage 18 into the inlets 9A, and then through the pin insertion mortises 9B into the capsule K. The air outflow passages 10 allows the air carrying powder type medication from the capsule K to release through the pin insertion mortises 10B into the outlets 10A and then towards the inhalation port 4.

Two supplementary air passages 11, 11 are prepared in the capsule holder 5 around the periphery of the capsule carrying chamber 8: each of the supplementary air passages 11 penetrates axially the substance of the capsule holder 5 at a position with a right angle apart from the foregoing air inflow and air outflow passages. Each of the supplementary air passage allows a supplementary inflow of air when the patient breathes in to draw in powder type medication, and relieves him of choking pain associated with the inhalation. Each of the supplementary air passages 11 is prepared as a straight tunnel with a diameter similar to those of the air inflow and air outflow passages 9 and 10: the supplementary air 11 is so designed as to allow air to pass through more smoothly than is possible with the air inflow and air outflow passages which take tortuous courses.

A small-sized hole 12 is axially prepared at the center of the capsule holder 5 on its mouth side to be continuous with the capsule carrying chamber 8. This small-sized hole 12 is prepared so that a tool is inserted through it to remove the capsule K from the capsule carrying chamber.

A cap 13 which forms a part of a lid body is mounted on the top of the holder carrier 3. The cap 13 forms a unit roughly comprising a disc-like cap body 14 whose diameter corresponds with that of the holder carrier 3, a supporting cone 15 which protrudes towards the mouth side with a taper, and a capsule stabilizer 16 which, when the cap is closed, holds the top of a capsule columnar in form placed in the capsule carrying chamber 8. From the supporting cone 15 protrudes a valve opening controller 17 towards top to control the opening of a below-described check valve 22. Around the periphery of the cap body 14, is prepared a hinge end 14A which joints with the bracket 3D of the holder carrier 3, while on the opposite side to the hinge end 14A, is formed a hook nail 14B which fits reversibly to the notch 3E.

Figure 8:
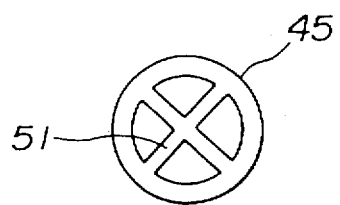
FIG. 8 is a plan view of the stopper seen along the arrow line VIII—VIII of the valve body carrying cylinder in FIG. 6.

The cap 13 is opened, as illustrated in FIG. 2, with the hinge fixed by the bracket 3D as a pivot so that a capsule K can be introduced into the capsule carrying chamber 8 or the capsule be taken out from the chamber. After a capsule has been placed properly in the capsule carrying chamber 8, as illustrated in FIG. 8, the hook nail 14B of the cap body 14 is jointed with the notch 3E to securely fix one end of the cap body 14 onto the holder carrier 3. In this state, the capsule stabilizer 16 enters into the capsule carrying chamber 8, and stabilizes the capsule K in the capsule carrying chamber 8, thereby preventing it from escaping.

A common air passage 18 is also provided according to the present embodiment. This common air passage 18 is formed by a valve body carrying chamber 19 bounded with the cap body 14, supporting cone 15 and capsule stabilizer 16, a top opening prepared at the center of the cap body 14 and interconnecting the valve body carrying chamber 19 and the atmosphere, and air inflow openings 21, 21, . . . which penetrate the supporting cone 15 to interconnect the valve body carrying chamber 19 with the air inflow passages 9 and supplementary passages 11. The air inflow openings 21 are prepared four (three of them being illustrated in the figure) with each 90 degree apart from each other to correspond with the air inflow passages and supplementary air inflow passages. The common air passage 18, when the patient draws in air through the inhalation port 4, acts as a passage to send the air towards the air inflow passages 9 and supplementary air inflow passages 11.

Figure 3:
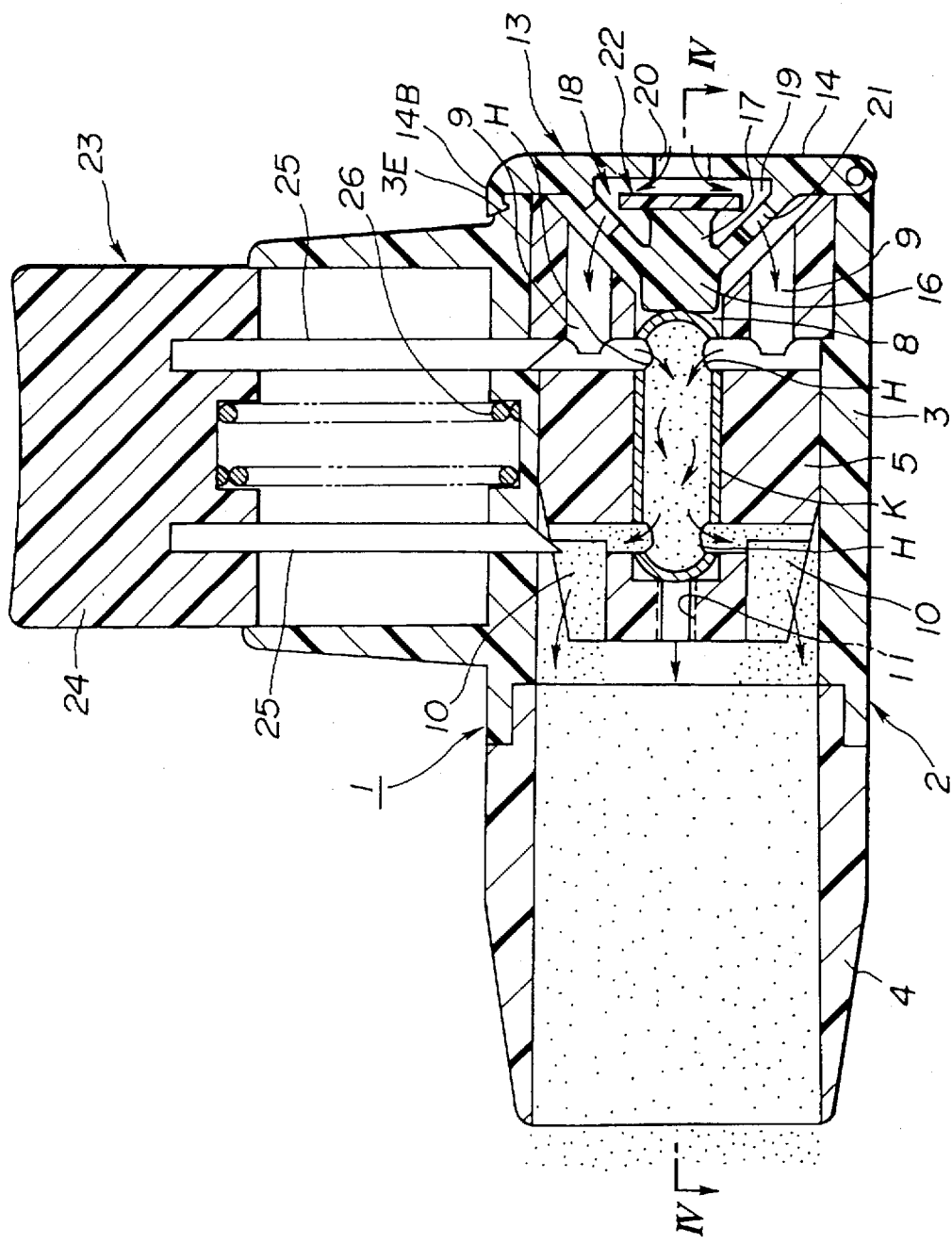
FIG. 3 is a still other sectional view seen from the same angle as in FIG. 1 which illustrates how powder in the capsule moves during inhalation.
Figure 4:
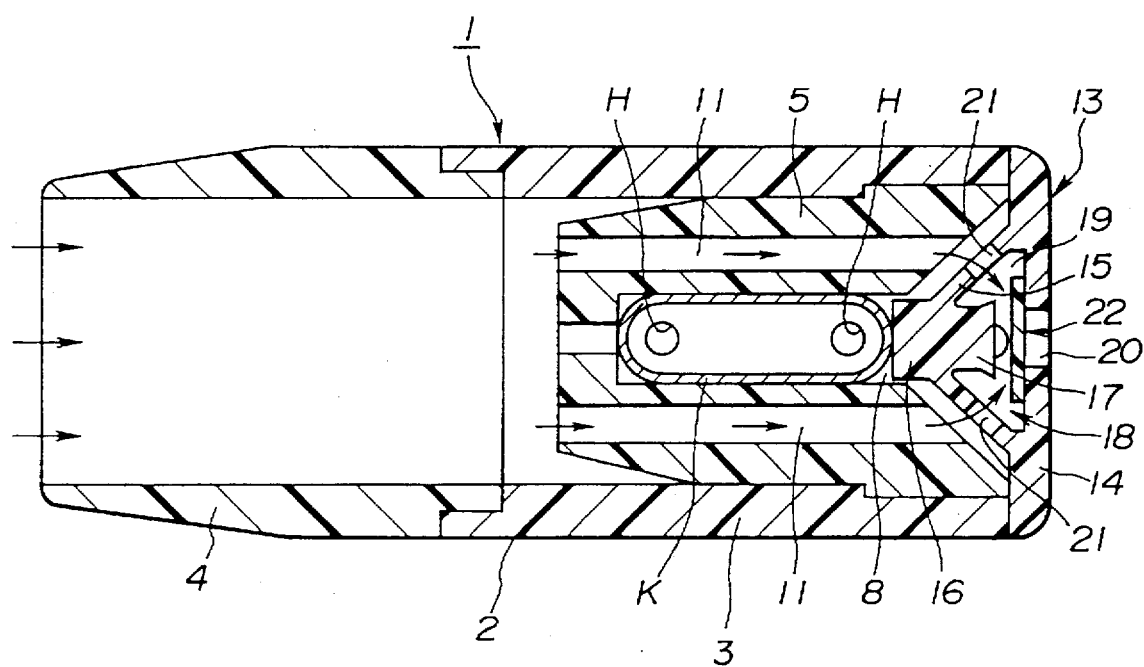
FIG. 4 is a fourth sectional view along the arrow line IV—IV in FIG. 3 which illustrates how counter air current produced in the inhalation port flows through the dispenser.

A disc-type check valve 22 is placed in the valve body carrying chamber 19 which forms a part of the common air passage 18. The check valve 22, when the patient draws in air through the inhalation port, opens, as illustrated in FIG. 3, under the pressure of the air flowing in through the top opening 20 and striking against the top of the valve opening controller 17, and permits the air to flow through air inflow passages 9 and supplementary air inflow passages 11. If, however, the patient falls to sudden coughing with the inhalation port 4 in his mouth, thereby blowing air out the inhalation port 4 to make a counter air flow, the check valve 22, as illustrated in FIG. 4, will be pressed, under the pressure of the air which flows into the valve body carrying chamber 19 through the supplementary air inflow passages 11 and air inflow openings 21, against the cap body 14, thereby closing the top opening.

A piercing member 23 is provided for easily puncturing holes through the capsule K placed in the capsule carrying chamber 8. The piercing member 23 comprises a support 24 which can slide into the guide cylinder 3A, pins 25, 25 each of which has one end or base fixed onto the support 24 and the other end with a sharp tip or needle 25A inserted into the pin mortise 3F or 3G, and a kickback spring 26 which is placed between the support 24 and the holder carrier 3. The kickback spring 26 is, after holes have been made through the body of the capsule K, to return the support 24 and pins 25 to their initial position where only the needles 25A are kept inserted in the pin insertion mortises 9B and 10B.

When the piercing member 23 is pressed in the face of the resistance from the kickback spring 26, the support 24 slides into the guide cylinder 3A, and the needles 25A penetrates a capsule K in the capsule carrying chamber 8. Thus, near the two ends of the capsule K along its axial length, are prepared in radial directions two penetrating holes H, H (see FIGS. 3 and 4) which interconnect the air inflow passages 9 with the air outflow passages 10. When the pressing force against the support 24 is released, the counterforce from the kickback spring 26 returns the support 24 and pins 25 to their initial positions.

The inhalation type medication delivery device of this invention has the above-described conststruction. Next, a description will be given of how the patient should prepare the device before inhalation of the powder type medication. Further, description will be given regarding the operation and functioning of the device during inhalation, including how powder type medication and air will flow through the inhalation type medication delivery device of the invention.

Firstly, preparations necessary for placement of a capsule K into the inhalation type medication delivery device and penetration of the capsule K will be described.

The patient should firstly open the cap 13, as illustrated in FIG. 2, and insert a capsule K from the top into the capsule carrying chamber 8. As the top end of the capsule holder 5, or the capsule insertion guide 6 forms a depression having an inverted-cone form in profile, the capsule can be easily introduced into the capsule carrying chamber 8. After the capsule K has been placed properly in the capsule carrying chamber 8, the jointing nail 14B of the cap body 14 is fitted to the notch 3E of the holder carrier 3, to fix the cap 13 to the holder carrier 3. After this operation, the capsule K in the capsule carrying chamber 8 is held firmly with the capsule stabilizer 8 to be kept stabilized in the capsule carrying chamber 8, and prevented from falling or escaping during drug dispensation.

To prepare penetrating holes H through the capsule K, the user should press the support 24 of the piercing member 23 into the guide cylinder 3A, thereby to insert pins 25 into respective pin insertion mortises 9B and 10B. Through this operation, the needles 25A of the pins 25 penetrate the capsule K in the capsule carrying chamber 8, to form four penetrating holes H which interconnect the air inflow passages 9 and air outflow passages 10. After four penetrating holes through the capsule K have been formed, the support 24 together with the pins 25 returns to the initial position by the counter force from the kickback spring 26.

Then, description will be given of how air and powder type medication will flow through the inhalation type medication delivery device of this invention while the patient inhales powder type medication.

Firstly, when the patient puts the inhalation port 4 in his mouth, and breathes in, air flows in, as illustrated in FIG. 3, by opening the valve of the check valve 22, into the common air passage 18, and then from the inlets 9A of the air inflow passages 9 through the pin insertion mortises 9B into the capsule carrying chamber 8 where air enters through the penetrating holes H, H on top side into the body of the capsule. Air flowing through the capsule forcibly diffuses powder type medication stored in the capsule, and incorporates it in itself.

The air in the capsule K with powder type medication dispersed within departs from the penetrating holes H, H on mouth side through the pin insertion mortises 10B communicating with the air outflow passages 10, to be released into the inhalation port 4. Then the air with powder type medication moves into the patient's mouth and then through the trachea into the interior of the lungs.

When the patient breathes in to inhale powder type medication, air is also allowed to flow from the common air passage 18 through the supplementary air passages 18 towards the inhalation port 4, and this additional air supply relieves the patient of choking pain associated with the inhalation. If, however, the patient falls to sudden coughing during inhalation, air blown out into the inhalation port 4 will take the courses as indicated by arrows in FIG. 4: one part of it passes through the air outflow passages 10, and the other part passes through the supplementary air passages 11. The supplementary air passages 11 are prepared as a straight tunnel with a diameter similar to those of the air inflow and air outflow passages 9 and 10: the supplementary air passage 11 is so designed as to allow air to pass through more smoothly than is possible with the air inflow and air outflow passages 9 and 10 which take tortuous courses. This construction allows the counter air current to flow more smoothly through the supplementary air passages 11.

Accordingly, the part of air flowing from the inhalation port 4 through the supplementary air passages 11 reaches the common air passage 18 faster than does the other part flowing through the air outflow and air inflow passages 9 and 10, thereby to press the check valve 22 against the cap body 14 to close the top opening before the arrival of the other part. Through this operation, the counter air current passing through the air inflow passages 10 reaches the common air passage 18 only to find the check valve 22 being closed, and hence the escape of powder type medication from the capsule K can be prevented.

As is evident from above description, according to this example, when the user draws in air from the inhalation port to inhale powder type medication, the check valve 22 placed at midway in the common air passage 18 opens, thereby allowing air with powder type medication dispersed within from a capsule K to pass through the air inflow and air outflow passages 9 and 10 into the patient's mouth. If, however, the patient falls to sudden coughing during inhalation while keeping the inhalation port 4 in his mouth, it will bring about a violent counter air flow into the inhalation port 4. This counter air current, being allowed to pass smoothly through the supplementary air passages 11, reaches quickly the common air passage 18 to close the check valve 22 there, thereby preventing the escape into the atmosphere of the counter air current passing through the air outflow and air inflow passages 10 and 9. As a part of air blown out by coughs can prevent, through the action of the valve, the escape into the atmosphere of powder type medication of the capsule K which passes through the air inflow passages 9 and common air passage 18, waste of powder type medication of the capsule K during inhalation can be minimized, which ensures efficient use of powder type medication.

Further, when the cap 13 is closed, the capsule stabilizer 16 fix the capsule K firmly in the capsule carrying chamber 8, to prevent it from falling or escaping. This allows easy and sanitary handling of the capsule during inhalation of powder type medication. As the cap 13 is hinged through a pivot with the holder carrier 3, loss of the cap 13 can be prevented.

Hereinbelow, a second preferred embodiment will be described with reference to FIGS. 5–10. This example is characterized by having check valves placed at midway of air inflow passages so that counter air currents can escape through supplementary air passages. In this example, the element corresponding in function with the counterpart in the first example described above will be represented by the same symbol, and its explanation omitted.

In the figures, 31 represents a dispenser body which forms the body of the present inhalation inhalation type medication delivery device. The dispenser body 31 comprises an dispenser body 32 and a capsule holder 34.

Figure 6:
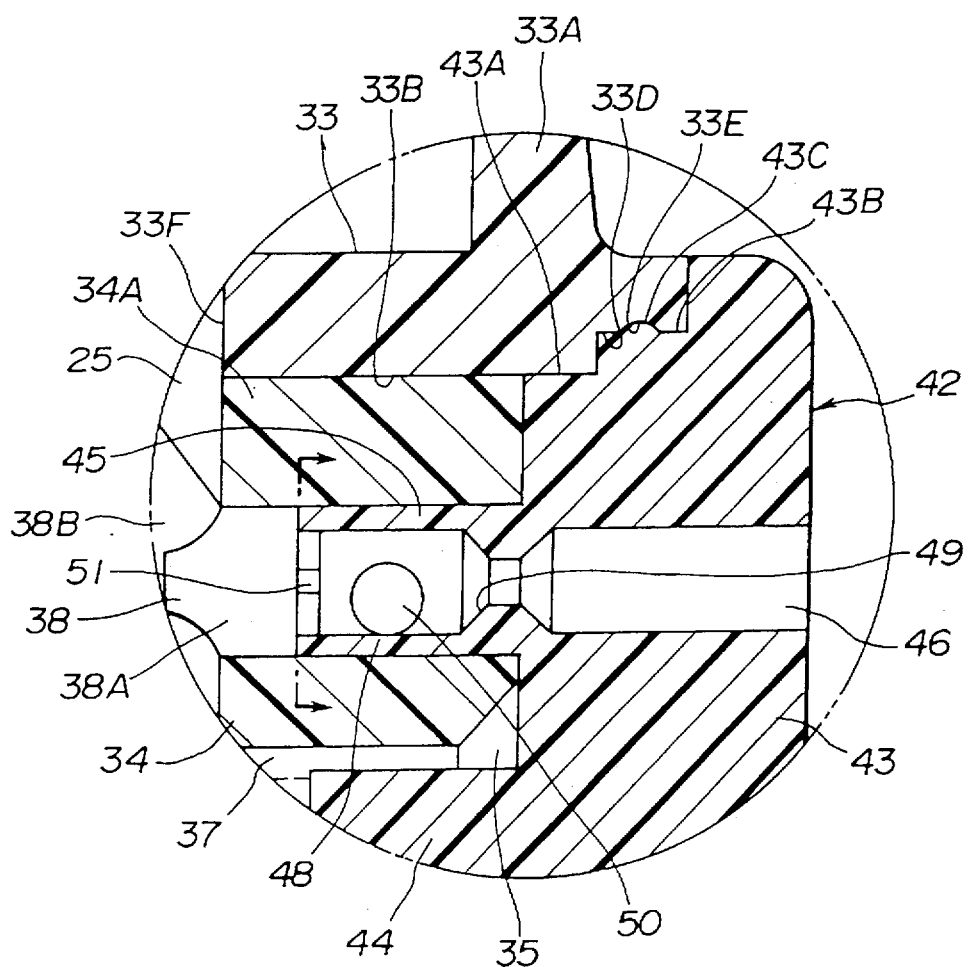
FIG. 6 is an enlarged view of the part indicated by arrow A in FIG. 5.

A main body of the dispenser 32 is substantially cylindrical, and a holder carrier 33 is provided which composes the dispenser body 32 together with an inhalation port 4. On the side wall of the holder carrier 33 is attached a guide cylinder 3 having an outward protruding mouth and supporting a support 24. On the top side is formed an annular step 33B which engages with a stopper 34A of the capsule holder 34, while on the mouth side, is formed another annular step 33C which engages with a fitting cylinder 4A of the inhalation port 4. In addition, around the periphery of top side of the holder carrier 33, as illustrated in FIG. 6, is prepared a trapping step 33D which joins with the fitting step 43B of a below-described cap body 43, and on the trapping step 33D is inscribed an annular groove 33E which engages with an annular elevation 43C. Through the holder carrier 33 penetrate pin holes 33F and 33G which communicate with pin insertion mortises 38B connecting with below-described air inflow passages 38 and with pin insertion mortises 39B connecting with air outflow passages 39, respectively.

A capsule holder 34 is inserted into the interior of the holder carrier 3. The capsule holder 34 is shaped practically like a column similarly to the above-described capsule holder 5, and has an annular stopper 34A formed on the periphery on top side which joins with the annular step 33B of the holder carrier 33. At the center of top side of the capsule holder 34, a hollow is prepared to form a capsule insertion guide 34 with a taper in profile. The periphery on mouth side of the capsule holder 34 has a tapering surface 36.

A powder retaining chamber 37 or a capsule carrying chamber which is prepared axially at the center of the capsule holder 34, and has a mouth on top side which communicates with a capsule insertion guide 35. The capsule carrying chamber 37 is to hold a capsule K inserted through the mouth on its top end, and is so constructed that, when the capsule has been put into place, its open mouth can be closed by a capsule stabilizer 44 of the cap 42. 38, 38 represent two air inflow passages prepared on top side of the capsule holder 34. Each of the air inflow passages 38 is composed of axially prepared inlets 38A, 38A and radially prepared pin insertion mortises 38B, 38B. Into each air inflow passage 38A is inserted a below-described a valve body carrying cylinder 45, and Each pin insertion mortise 38B communicates with the corresponding pin mortise 33F prepared in the wall of the holder carrier 33.

Two air outflow passages 39, 39 are formed on mouth side of the capsule holder 34. The air outflow passages 39, 39 are composed each of two components, or outlets 39A, 39A and pin insertion mortises 39B, 39B: the outlet 39A is prepared by removing part of the tapering wall 36, and the pin insertion mortise 39B is so prepared as to communicate with the corresponding pin mortise 33G prepared in the wall of the holder carrier 33.

Two supplementary air passages 40, 40 are prepared in the capsule holder 34 (only one of them illustrated in the figures): each of the supplementary air passages 11 penetrates axially the substance of the capsule holder 34 at a position with a right angle apart from the air inflow and air outflow passages 38 and 39.

A small-sized hole 41 is axially prepared at the center of the capsule holder 5 on its mouth side.

A cap 42 forms a part of a lid body mounted on the top of the holder carrier 33 of this example. The cap 42 consists roughly of a thick, disc-form cap body 43, a capsule stabilizer 44 columnar in form which protrudes from the cap body 43 towards the mouth side and, when the cap 42 closes, invades into the capsule carrying chamber 37, and valve body carrying cylinders 45, 45 which are placed at the periphery of the capsule holder 44, protrude axially towards the mouth side, and fit into the inlets 38A of the air inflow passages 38. Around the outer rim of the cap body 43 are prepared the fitting step 43A to fit to the annular step 33B of the holder carrier 33, the fitting step 43B outer than the fitting step 43A to fit to the trapping step 33D, and the annular elevation 43C prepared around the circumference flush with the fitting step 43B to reversibly fit to the annular groove 33E.

Figure 5:
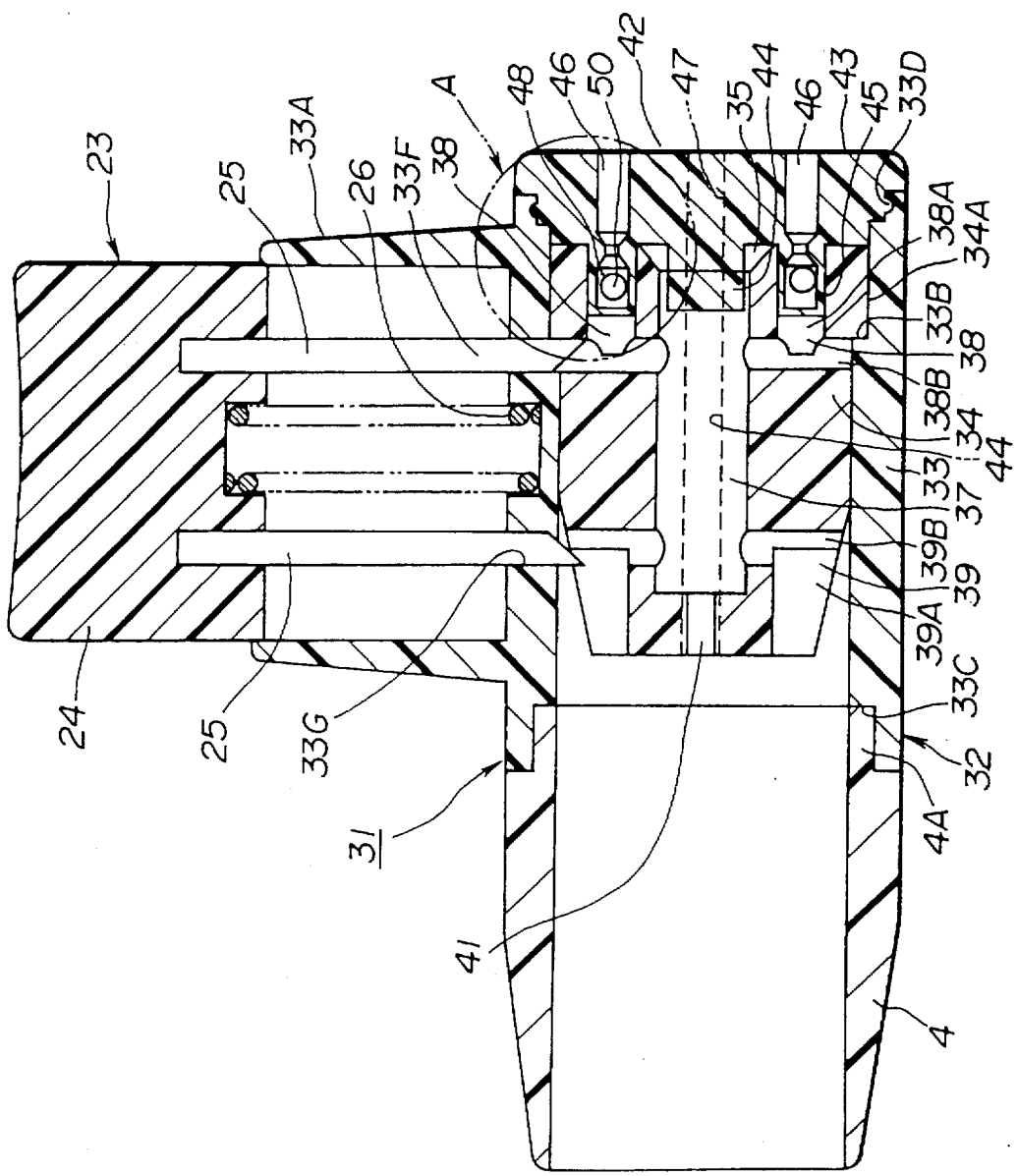
FIG. 5 is a sectional view of the inhalation type medication delivery device of the second preferred embodiment according to this invention.
Figure 7:
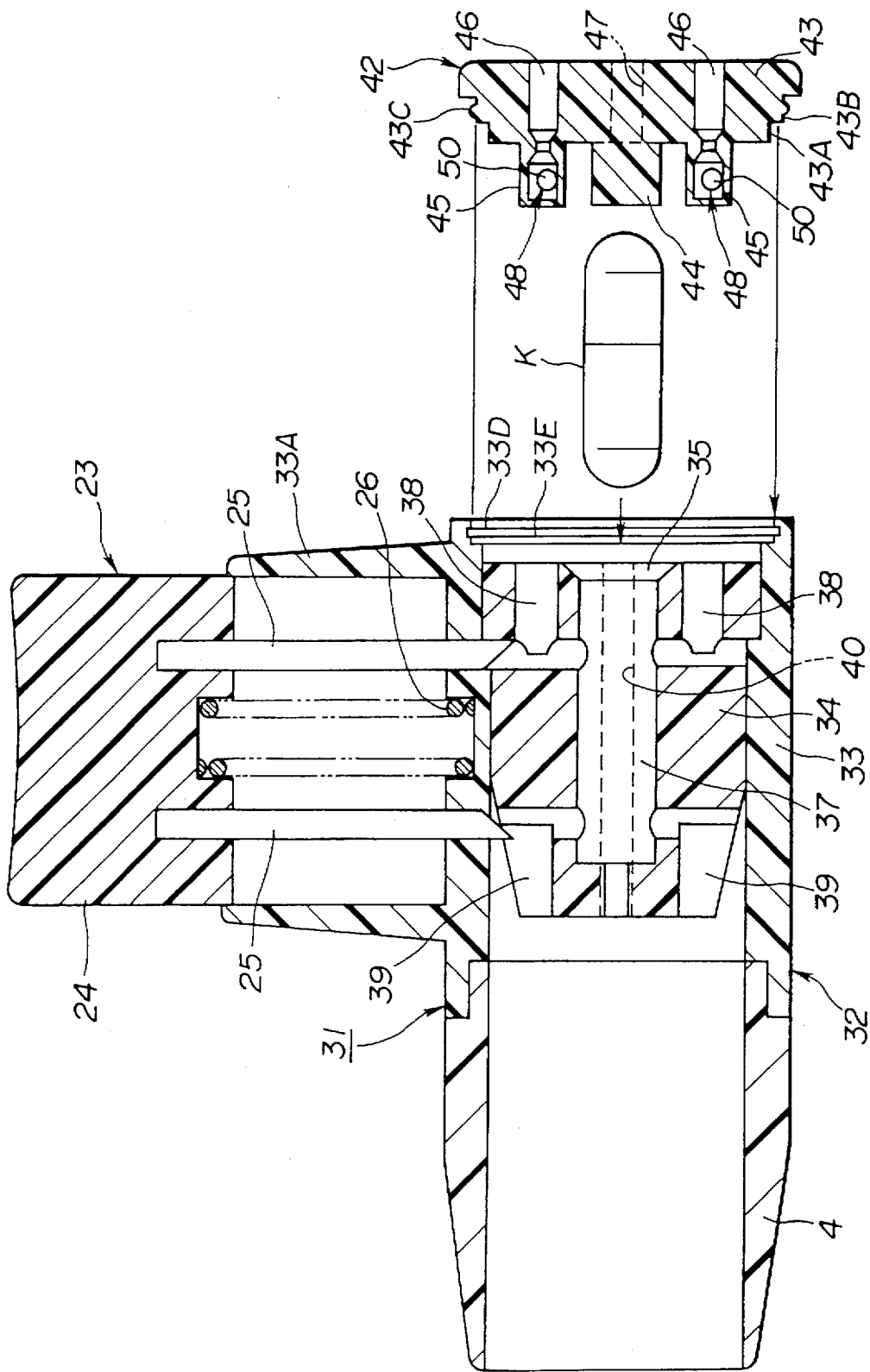
FIG. 7 is another sectional view seen from the same angle as in FIG. 5 which illustrates how the cap is removed so that a capsule can be inserted into the capsule carrying chamber.

The cap 42 can be removed, as illustrated in FIG. 7, from the holder carrier 33 when it is necessary to introduce a capsule K into the capsule carrying chamber 37 or to take out the capsule K from the chamber. After a capsule has been placed properly in the capsule carrying chamber 37, as illustrated in FIG. 5, the fitting step 43A is allowed to fit to the annular step 33B and the fitting step 43B to fit to the annular step 33B, thereby to engage the annular elevation 43C with the annular groove 33E, so that the top end of the holder carrier 33 is closed. In this state, the capsule stabilizer 44 enters into the capsule carrying chamber 37, to fix firmly the capsule K in the capsule carrying chamber 37 thereby preventing the capsule from falling or escaping.

Two air inlets 46, 46 are prepared axially in the cap body 43 so as to correspond with the respective valve body carrying chambers 45, and form part of the respective air inflow passages 38. The air inlet 46 axially penetrates the cap body 43 to be continuous with the valve body carrying cylinder 45. The air inlet 46 interconnects the atmosphere with the air inflow passage 38.

Two supplementary air inlets 47, 47 are prepared eccentrically in the capsule holder 43 and forming part of two supplementary air passages 40 (only one of them illustrated in the figures): each of the supplementary air inlet 47 penetrates axially the substance of the cap body 43 at a position with a right angle apart from the air inlet 46. The supplementary air inlet 47 always interconnects the supplementary air passage 40 with the atmosphere.

48, 48 represent check valves of this example installed in the respective valve body carrying cylinders 45 on the mouth side of the respective air inlets 46. The check valve 48, as illustrated in FIG. 6, consists roughly of a valve seat 49 which results from the constriction of the air inlet 46, a spherical valve body 50 which is so placed on the mouth side of the valve seat 49 as to move freely in the space within the valve body carrying cylinder 45, and a stopper 51 which is placed on the mouth side of the valve body carrying cylinder 45 to limit the movement of the spherical valve body. The stopper, as illustrated in FIG. 8, has a cross structure to allow the passage of air. The spherical valve body 50 is made of a light synthetic resin or the like so that it can easily move under the influence of air passage through the air inlet 46.

Figure 9:
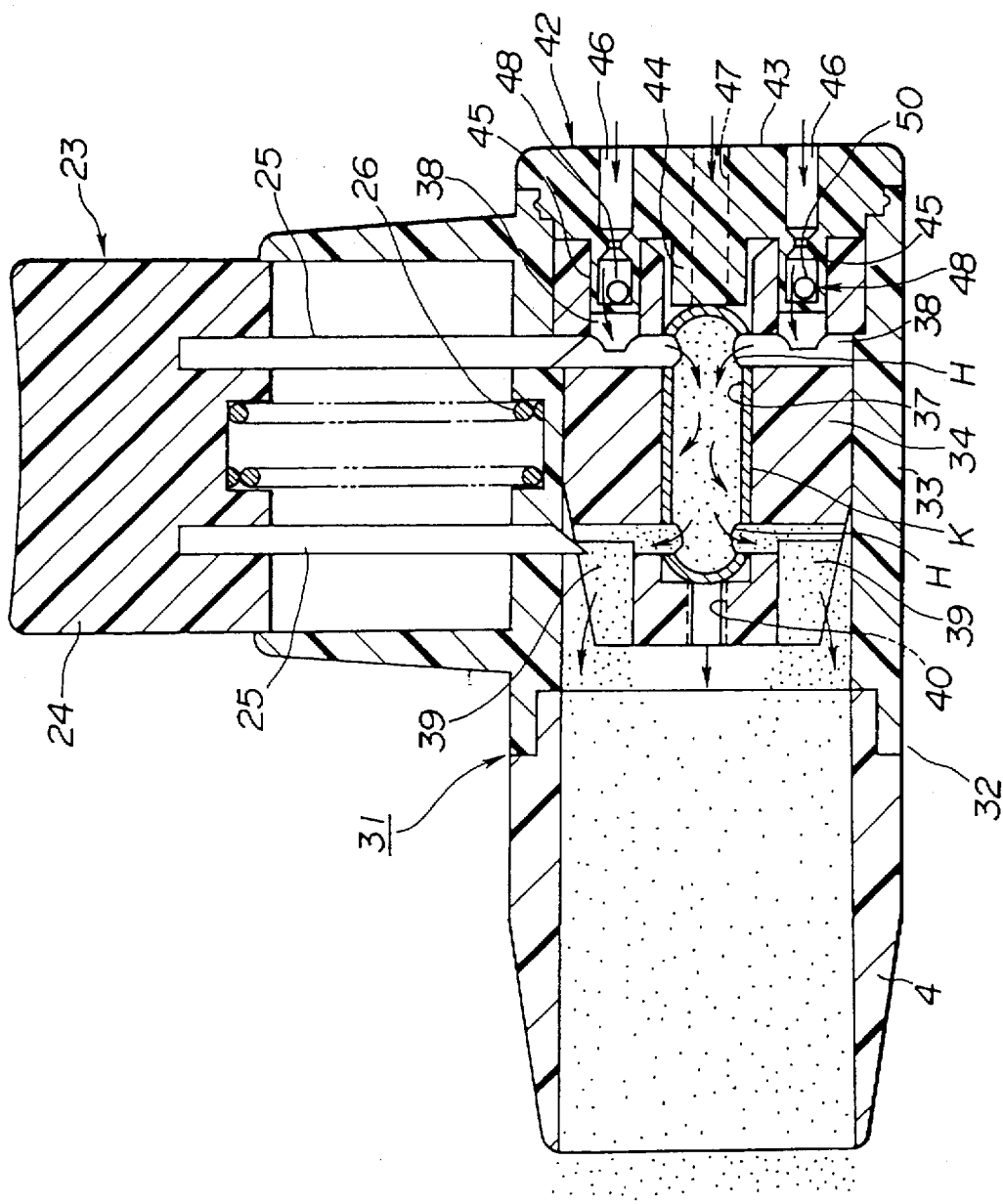
FIG. 9 is still another sectional view seen from the same angle as in FIG. 5 which illustrates how powder type medication in the capsule moves during inhalation.
Figure 10:
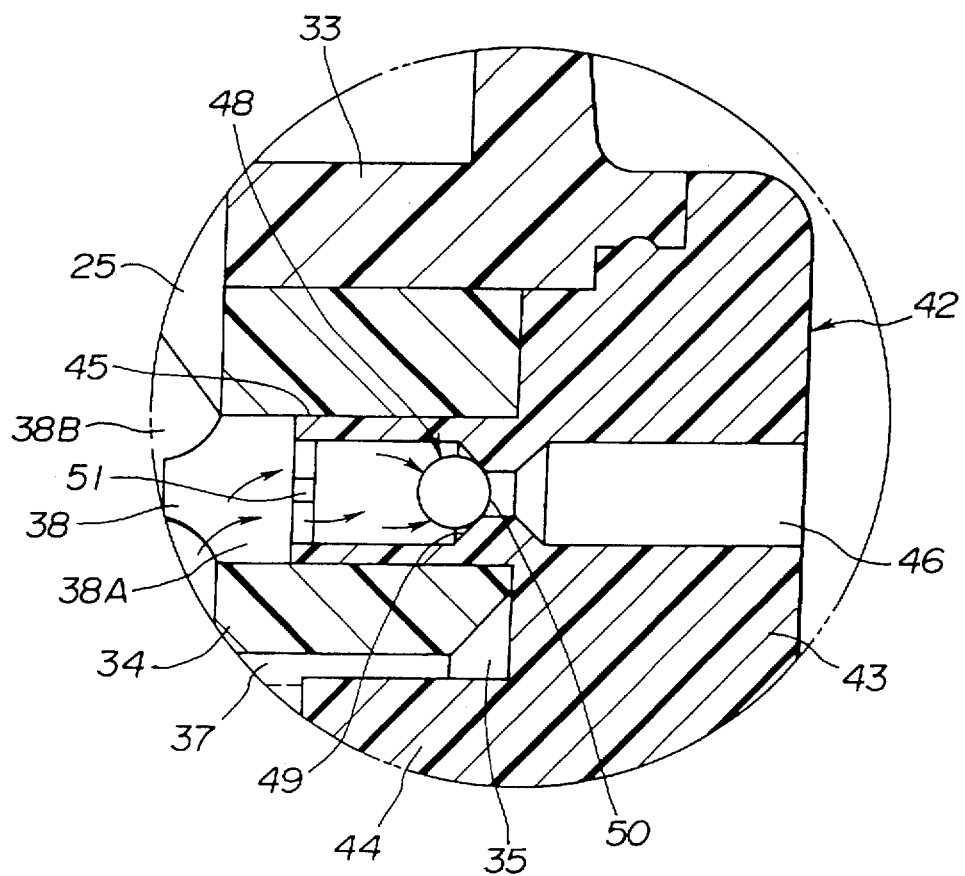
FIG. 10 is an enlarged view of the check valve seen from the same angle as in FIG. 6 which illustrates how the check valve operates when a counter air current is produced in the inhalation port.

The check valve 48 with such construction allows, when the user draws in air through the inhalation port 4, the spherical valve body 50 to move towards mouth side by virtue of air inflow through the air inlet 46, and to be held against the stopper 51 as is illustrated in FIG. 9. In this state the valve is kept open and air is allowed to flow into the air inflow passage 38. If, however, the patient falls to sudden coughing during inhalation while keeping the inhalation port 4 in his mouth, which brings about a violent counter air flow into the inhalation port 4, following events will take place in succession. The counter air current passes through the air inflow passage 38 into the air inlet 46 as illustrated in FIG. 10, and this air inflow moves the spherical valve body 50 towards top side, and holds it against the valve seat 49, thereby closing the entry to the air inlet 46. This prevents powder type medication from escaping even during outbursts of counter air current.

In this example with the construction as described above, the same advantage can be obtained as from the first example. Particularly, as this example has the check valves 48 installed in series with the air inlets 38, and the supplementary air passages 40 interconnecting the atmosphere and the inhalation port 4, the check valves 48 can prevent escape of powder type medication of a capsule K driven by counter air flow which might arise as a result of patient's coughing. Then, the counter air flow, finding no way to escape before the closed check valve 48, flows through the supplementary air passage 40 into the atmosphere. This maneuver prevents outbursts of counter air current often associated with coughing from blowing out the present inhalation type medication delivery device, thereby contributing to easy and sanitary handling of this inhalation type medication delivery device.

In the first example, the cap 13 is attached through a pivot to the holder carrier 3 so that the cap can be freely opened and closed. But the present invention is not limited only to this type of attachment. The cap may be made as a unit with the holder carrier with a thin hinge between the two, so that the cap can be freely moved. Or, the cap can be reversibly fitted to or screwed in the holder carrier.

In the second example, the cap 42 is reversibly fitted to the holder carrier 33 by engaging the annular elevation 43C with the annular groove 33E. But, as in the first example, the cap may be attached to the holder carrier through a pivot.

In the above examples, air passages through which powder type medication is delivered (air inflow passages 9, 38 and air outflow passages 10, 39), and supplementary air passages 11, 40 number 2 each. But, this invention is not limited to this number, and air passages can be any number as appropriate, for example, one, four, etc., according to the inhalation capacity of the patient (the pulmonary vital capacity).

In the above examples, the capsule carrying chamber 8, 37 is prepared to hold a capsule K filled with powder type medication. Instead of this, for example, a powder containment chamber may be prepared in the body of the inhalation type medication delivery device, and powder type medication instead of a capsule may be directly introduced into this chamber, to be inhaled.

In the above examples, the holder carrier 3, 33 is provided with the fitting step 3C, 33C and the inhalation port 4 with the fitting cylinder 4A. This construction allows the inhalation port 4 to be reversibly attached to the holder carrier through the fitting step 3, 33C and the fitting cylinder 4A. But, the inhalation port may be reversibly screwed into the holder carrier, or may be reversibly attached to the holder carrier through a pin-groove joint.

[Operation]

As detailed above, according to the invention set forth in the preferred embodiment, when the powder type medication is introduced into the powder containment chamber, the lid covering the powder containment chamber is opened, the powder type medication is introduced into the powder containment chamber, and then the lid is closed. Such storing method prevents fall or escape of the powder type medication from the powder containment chamber, thereby ensuring easy and economical handling of the powder type medication. When ingesting the powder type medication stored in the powder containment chamber through inhalation, the patient puts the inhalation port into the mouth, and breathes in air. Then, he can draw in the powder type medication in the powder containment chamber through the inhalation port into the lungs. If, on the other hand, the patient falls to sudden coughing while keeping the inhalation port in his mouth, and a violent counter air flow is produced in the inhalation port, the air current will flow through air passages in an opposite way to normal. At that time, however, the check valve installed in the lid will be put to closure, to block the air passages, which will prevent the powder type medication in the powder containment chamber from escaping into the atmosphere. As a result, waste of powder type medication in the powder containment chamber will be avoided and efficient ingestion of powder type medication achieved. This ensures administration of a prescribed amount of powder type medication to the patient, which will facilitate the full development of drug efficacy.

Further, the first embodiment provides a modification whereby the inhalation type medication delivery device body is provided with supplementary air passages which interconnect the atmosphere and the inhalation port independently of the air passages, thereby allowing entry of additional air during inhalation of powder type medication. This helps the patient inhale a greater volume of air than is possible otherwise, which will contribute to relieving him of choking pain often associated with inhalation of powder type medication.

According to the invention as set forth in the second embodiment, when a capsule filled with powder type medication is introduced into the capsule carrying chamber, the lid covering the capsule carrying chamber is opened, the capsule is introduced into the capsule carrying chamber, and then the lid is closed. Such storing method prevents fall of the capsule from the capsule carrying chamber, thereby ensuring easy and sanitary handling of the capsule. When ingesting powder type medication of the capsule in the capsule carrying chamber through inhalation, the patient prepares, using the piercing member, penetrating holes through the capsule in the capsule carrying chamber, of which one communicates with the air inflow passage and the other with air outflow passage, then puts the inhalation port into the mouth, and breathes in air. By this operation, he allows air to enter through the air inflow passage into the capsule, and then the air with powder type medication dispersed within to pass from the air outflow passage through the inhalation port into the lungs. If, on the other hand, the patient falls to sudden coughing while keeping the inhalation port in his mouth, and a violent counter air flow is produced in the inhalation port, the air current will flow in an opposite way to normal from the air outflow passages through the capsule towards the air inflow passages. At that time, however, the check valve installed in the lid will be put to closure, to block the air inflow passages, which will prevent powder type medication in the capsule from escaping into the atmosphere. As a result, waste of powder type medication in the capsule will be avoided and efficient ingestion of powder type medication achieved. This ensures administration of a prescribed amount of powder type medication to the patient, which will facilitate the full development of drug efficacy.

Also according to the final embodiment as described above, when a powder type medication is introduced into the powder containment chamber, the lid covering the powder containment chamber is opened, the powder type medication is introduced into the powder containment chamber, and then the lid is closed. Such storing method prevents fall or escape of the powder type medication from the powder containment chamber, thereby ensuring easy and sanitary handling of the powder type medication. When ingesting the powder type medication stored in the powder containment chamber through inhalation, the patient puts the inhalation port into the mouth, and breathes in air. By this operation, he allows air entering the common air passage to pass through the air inflow passages into the powder containment chamber, and then the powder type medication in that powder containment chamber to flow from the air outflow passages through the inhalation port into the lungs. While the patient ingests powder type medication through inhalation, air is allowed to pass from the common air passage through supplementary air passages into the inhalation port. This enables the patient to inhale a sufficient volume of air according to his pulmonary vital capacity, which will contribute to relieve him of choking pain often associated with inhalation of powder type medication. If, on the other hand, the patient falls to sudden coughing while keeping the inhalation port in his mouth, and a violent counter air flow is produced in the inhalation port, the air current will flow in an opposite way to normal from the air outflow passages through the powder containment chamber towards the air inflow passages. At that time, however, the check valve installed in the lid will be put to closure, to block the air inflow passages, which will prevent the powder type medication in the powder containment chamber from escaping into the atmosphere. As a result, waste of powder type medication in the powder containment chamber will be avoided and efficient ingestion of powder type medication achieved. This ensures administration of a prescribed amount of powder type medication to the patient, which will facilitate the full development of drug efficacy.

The present invention in not limited only to the description as herein disclosed but may be modified and embodied in other ways without departing from the scope or inventive concept of the invention as set forth above.

What is claimed:

1. An inhalation medication delivery device comprising:
   a dispenser body which has a powder containment chamber disposed at a first axial side thereof and an inhalation port for drawing in a powder medication on a second axial side thereof;
   a lid for opening/closing said powder containment chamber;
   an air passage defined in said dispenser body for allowing introduction of a powder medication in said powder containment chamber of said dispenser body into an airflow toward said inhalation port according to a suction force generated by inhalation, one end of said air passage opening through said lid towards ambient atmosphere and another end of which communicates through said powder containment chamber with said inhalation port; and
   a check valve which is installed into said lid to prevent air drawn into said inhalation port from flowing through said air passage towards ambient atmosphere.

2. An inhalation powdered medication delivery device as set forth in claim 1, wherein said lid is attached to one side of the dispenser body.

3. An inhalation medication delivery device as described in claim 1, in which said dispenser body includes a supplementary passage which communicates between said inhalation port and said ambient atmosphere independently of said air passage, so as to generate a supplementary air suction action during inhalation of powder medication.

4. An inhalation medication delivery device as described in claim 1, further including a second air passage defined in said dispenser body and having a first end thereof disposed at said powder containment chamber, a second end thereof being formed so as to communicate with said inhalation port.

5. An inhalation medication delivery device as described in claim 4, further including a supplementary passage which communicates between said inhalation port and said ambient atmosphere independently of said first and second air passages, so as to generate a supplementary air suction action during inhalation of powder medication.

6. An inhalation medication delivery device as described in claim 5, further including a common air passage formed in said lid and having a first end thereof opening to said ambient atmosphere and a second end thereof in communication with said first, second and supplementary air passages.

7. An inhalation powdered medication delivery device comprising:
   a dispenser body including a capsule carrying chamber disposed at a first axial end thereof for retaining a capsule filled with a powder medication and, an inhalation port for facilitating inhalation of said powder medication formed at a second axial end of said dispenser body;
   a lid for opening/closing said powder containment chamber;
   an air inflow passage defined in said dispenser body such that a first end thereof opens through said lid towards ambient atmosphere and a second end thereof is communicated with said inhalation port;
   piercing means attached to said dispenser body; and
   a capsule insertable in said capsule carrying chamber, said capsule having an opening defined therein according to utilization of said piercing means, said opening so formed as to establish communication between an interior of said capsule and a portion of said air inflow passage when said capsule is positioned in said capsule carrying chamber;

a check valve provided at said lid to prevent air drawn into the inhalation port from flowing through said air inflow passage in a direction other than an air inflow direction.

8. An inhalation powdered medication delivery device as set forth in claim 7, wherein said lid is attached to one side of the dispenser body.

9. An inhalation medication delivery device as described in claim 8, in which said dispenser body includes a supplementary passage which communicates between said inhalation port and said ambient atmosphere independently of said air passage, so as to generate a supplementary air suction action during inhalation of said powder medication.

10. An inhalation powdered medication delivery device comprising:

a dispenser body including a powder containment chamber disposed at a first axial end thereof, and an inhalation port for facilitating inhalation of a powder medication formed at a second axial end thereof;

a lid for opening/closing said powder containment chamber;

an air inflow passage defined in said dispenser body and having a first end thereof disposed at said lid so as to be communicated with ambient atmosphere, a second end thereof being formed so as to communicate with said inhalation port;

an air outflow passage defined in said dispenser body and having a first end thereof disposed at said powder containment chamber, a second end thereof being formed so as to communicate with said inhalation port;

a supplementary passage which communicates between said inhalation port and ambient atmosphere independently of said air inflow and said air outflow passages, so as to generate a supplementary air suction action during inhalation of powder medication;

a common air passage formed in said lid and having a first end thereof opening to ambient atmosphere and a second end thereof in communication with said air inflow, air outflow and supplementary air passages; and a check valve installed into said lid and placed substantially midway along said common air passage, to prevent air drawn into the inhalation port from flowing from said air outflow passage through said powder containment chamber or through said air inflow passage toward ambient atmosphere.

11. An inhalation powdered medication delivery device as set forth in claim 10, wherein said lid is attached to one side of the dispenser body.

* * * * *